(12) United States Patent
Bach et al.

(10) Patent No.: US 6,448,284 B1
(45) Date of Patent: Sep. 10, 2002

(54) SUBSTITUTED TRICYCLICS

(75) Inventors: Nicholas James Bach; Daniel Jon Sall, both of Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/868,975

(22) PCT Filed: Nov. 30, 1999

(86) PCT No.: PCT/US99/28407

§ 371 (c)(1),
(2), (4) Date: Jun. 20, 2001

(87) PCT Pub. No.: WO00/37472

PCT Pub. Date: Jun. 29, 2000

Related U.S. Application Data

(60) Provisional application No. 60/113,316, filed on Dec. 22, 1998.

(51) Int. Cl.[7] ................... C07D 487/00; A61P 29/00; A61K 31/403

(52) U.S. Cl. ........................ 514/411; 548/428

(58) Field of Search .......................... 548/428; 514/411

(56) References Cited

FOREIGN PATENT DOCUMENTS

| EP | 0 620 214 | 10/1994 |
|---|---|---|
| EP | 0 620 215 | 10/1994 |
| EP | 0 675 110 | 10/1995 |
| EP | 0839 806 A1 * | 5/1998 |

OTHER PUBLICATIONS

Edstrom et al Tetrahedron, vol. 53, No. 13, pp. 4549–4560, 1997.*

Ouyang et al Biochemistry 2000, 39, 5817–5830.*

* cited by examiner

Primary Examiner—Joseph K. McKane
Assistant Examiner—Kamal Saeed
(74) Attorney, Agent, or Firm—Francis O. Ginah; Arleen Palmberg

(57) ABSTRACT

A class of tricycles is disclosed together with the use of such for inhibiting $Spla_2$ mediated release of fatty acids for the treatment of conditions such as septic shock.

21 Claims, No Drawings

SUBSTITUTED TRICYCLICS

CROSS-REFERENCE TO RELATED APPLICATIONS

This application is a 371 of PCT/US99/28407 filed Nov. 30, 1999 which claims priority to provisional application Ser. No. 60/113,316 filed Dec. 22, 1998.

FIELD OF THE INVENTION

This invention relates to novel substituted tricyclic organic compounds useful for inhibiting $sPLA_2$ mediated release of fatty acids for conditions such as septic shock.

BACKGROUND INFORMATION

The structure and physical properties of human non-pancreatic secretory phospholipase $A_2$ (hereinafter called, "$sPLA_2$") has been thoroughly described in two articles, namely, "Cloning and Recombinant Expression of Phospholipase $A_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; The Journal of Biological Chemistry, Vol. 264, No. 10, Issue of Apr. 5, pp. 5335–5338, 1989; and "Structure and Properties of a Human Non-pancreatic Phospholipase $A_2$" by Kramer, Ruth M.; Hession, Catherine; Johansen, Berit; Hayes, Gretchen; McGray, Paula; Chow, E. Pingchang; Tizard, Richard; and Pepinsky, R. Blake; The Journal of Biological Chemistry, Vol. 264, No. 10, Issue of Apr. 5, pp. 5768–5775, 1989; the disclosures of which are incorporated herein by reference.

It is believed that $sPLA_2$ is a rate limiting enzyme in the arachidonic acid cascade which hydrolyzes membrane phospholipids. Thus, it is important to develop compounds which inhibit $sPLA_2$ mediated release of fatty acids (e.g., arachidonic acid). Such compounds would be of value in general treatment of conditions induced and/or maintained by overproduction of $sPLA_2$ such as septic shock, adult respiratory distress syndrome, pancreatitis, trauma-induced shock, bronchial asthma, allergic rhinitis, rheumatoid arthritis, etc.

It is desirable to develop new compounds and treatments for $sPLA_2$ induced diseases.

SUMMARY OF THE INVENTION

This invention provides tricyclic compounds as depicted in the general formula (I) below:

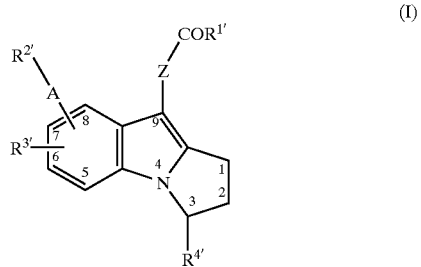

(I)

wherein;

Z is —C═O, —CH$_2$,

A is —O(CH$_2$)$_f$—; —NH(CH$_2$)$_f$—; —S(CH$_2$)$_f$—; —(CH$_2$)$_f$, where f is 1 to 3; —CH═CH—;

—C≡C—;

or —(L$_a$)—, where —(L$_a$)— is an acid linker having an acid linker length of 1 to 7;

R$^{1'}$ is —NHNH$_2$ or —NH$_2$;

R$^{2'}$ is —CO$_2$H; —CO$_2$(C$_1$–C$_4$)alkyl;

where R$^6$ and R$^7$ are each independently —OH or —O(C$_1$–C$_4$)alkyl; tetrazolyl; —CONR$^9$R$^{10}$, where R$^9$ and R$^{10}$ are independently hydrogen, —CF$_3$, —(C$_1$–C$_4$)alkyl, phenyl or —(C$_1$–C$_4$)alkylphenyl; —SO$_2$R$^{15}$; —CONHSO$_2$R$^{15}$, where R$^{15}$ is hydrogen, aryl, —(C$_1$–C$_6$)alkyl or —CF$_3$; or phenyl substituted with —CO$_2$H or —CO$_2$(C$_1$–C$_4$)alkyl;

R$^{3'}$ is selected from non-interfering substituents, carbocyclic radicals, carbocyclic radicals substituted with non-interfering substituents, heterocyclic radicals, and heterocyclic radicals substituted with non-interfering substituents;

R$^{4'}$ is selected from groups (a) and (b) where;
  (a) is —(C$_5$–C$_{20}$)alkyl, —(C$_5$–C$_{20}$)alkenyl, —C$_5$–C$_{20}$) alkynyl, carbocyclic radicals, or heterocyclic radicals, or
  (b) is a member of (a, substituted with one or more independently selected non-interfering substituents;

or a pharmaceutically acceptable racemate, solvate, optical isomer, prodrug derivative or salt thereof.

These substituted tricyclics are effective in inhibiting human $sPLA_2$ mediated release of fatty acids.

This invention is also a pharmaceutical formulation comprising a compound of formula I in association with one or more pharmaceutically acceptable diluteness, carriers and excipients.

This invention is also a method of inhibiting $sPLA_2$ comprising administering to a mammal in need of such treatment a therapeutically effective amount of a compound of formula I.

According to a further aspect of the present invention, there is provided a method of selectively inhibiting $sPLA_2$ in a mammal in need of such treatment comprising administering to said mammal a therapeutically effective amount of a compound of formula I.

This invention, further provides a compound of Formula I for use as a medicament in the treatment of inflammatory diseases such as sepsis, septic shock, adult respiratory distress syndrome, pancreatitis, trauma-induced shock, asthma, rheumatoid arthritis, osteoarthritis, acute bronchitis, chronic bronchitis, Inflammatory Bowel Disease, apoptosis, stroke, cystic fibrosis, allergic rhinitis, acute bronchiolitis, chronic bronchiolitis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing) miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus eryzhrematosis, or relapsing polychondritis and related diseases which comprises administering to a mammal in need of such treatment a therapeutically effective amount of the compound of formula I in an amount sufficient to inhibit sPLA$_2$ mediated release of fatty acid and to thereby inhibit or prevent the arachidonic acid cascade and its deleterious products.

Other objects, features and advantages of the present invention will become apparent from the subsequent description and the appended claims.

DETAILED DESCRIPTION OF THE INVENTION

Definitions

As used herein, the term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, tert butyl, n-pentyl, isopentyl, neopentyl, heptyl, hexyl, octyl, nonyl, decyl, undecyl, dodecyl, tridecyl, tetradecyl and the like. The term "alkyl" includes —$(C_1-C_2)$alkyl, —$(C_1-C_4)$alkyl, —$(C_1-C6)$alkyl, —$(C_5-C_{14})$alkyl, and —$(C_1-C_{10})$alkyl.

The term "alkenyl" as used herein represents an olefinically unsaturated branched or linear group having at least one double bond. Examples of such groups include radicals such as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl as well as dienes and trienes of straight and branched chains.

The term "alkynyl" denotes such radicals as ethynyl, propynyl, butynyl, pentynyl, hexynyl, heptynyl as well as di- and tri-ynes.

The term "halo" means chloro, fluoro, bromo or iodo.

The term "—$(C_1-C_4)$alkoxy", as used herein, denotes a group such as methoxy, ethoxy, n-propoxy, isopropoxy, n-butoxy, t-butoxy and like groups, attached to the remainder of the molecule by the oxygen atom.

The term "phenyl($C_1-C_4$)alkyl" refers to a straight or branched chain alkyl group having from one to four carbon atoms attached to a phenyl ring which chain is attached to the remainder of the molecule. Typical phenylalkyl groups include benzyl, phenylethyl, phenylpropyl, phenylisopropyl, and phenylbutyl.

The term "aryl" means an aromatic carbocyclic structure having six to ten carbon atoms. Examples of such ring structures are phenyl, naphthyl and the like.

The term, "heterocyclic radical", refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyridyl, thienyl, fluorenyl, pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo (1.2-A)pyridinyl, benzotriazolyl, anthranilyl, 1,2-benzisoxazolyl, benzoxazolyl, benzothiazolyl, purinyl, pryidinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, and quinoxalinyl.

The term "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, naphthyl, norbornanyl, bicycloheptadienyl, tolulyl, xylenyl, indenyl, stilbenyl, terphenylyl, diphenylethylenyl, phenylcyclohexeyl, acenaphthylenyl, and anthracenyl, biphenyl, bibenzylyl and related bibenzylyl homologues represented by the formula (bb),

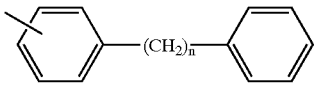

(bb)

where n is an integer from 1 to 8.

The term, "non-interfering substituent", refers to radicals suitable for substitution at positions 5 or 6 on the tricyclic nucleus (as depicted in Formula I) and radical(s) suitable for substitution on the heterocyclic radical and carbocyclic radical as defined above. Illustrative non-interfering radicals are hydrogen, —$(C_1-C_{14})$alkyl, —$(C_2-C_6)$alkenyl, —$(C_2-C_6)$alkynyl, —$(C_7-C_{12})$aralkyl, —$(C_7-C_{12})$alkaryl, —$(C_3-C_8)$cycloalkyl, —$(C_3-C_8)$cycloalkenyl, phenyl, tolulyl, xylenyl, biphenyl, —$(C_1-C_6)$alkoxy, —$(C_2-C_6)$alkenyloxy, —$(C_2-C_6)$alkynyloxy, —$(C_1-C_{12})$alkoxyalkyl, —$(C_1-C_{12})$alkoxyalkyloxy, —$(C_1-C_{12})$alkylcarbonyl, —$(C_1-C_{12})$alkylcarbonylamino, —$(C_1-C_{12})$alkoxyamino, —$(C_1-C_{12})$alkoxyaminocarbonyl, —$(C_1-C_{12})$alkylamino, —$(C_1-C_6)$alkylthio, —$(C_1-C_{12})$alkylthiocarbonyl, —$(C_1-C_6)$alkylsulfinyl, —$(C_1-C_6)$alkylsulfonyl, —$(C_1-C_6)$haloalkoxy, —$(C_1-C_6)$haloalkylsulfonyl, —$(C_1-C_6)$haloalkyl, —$(C_1-C_6)$hydroxyalkyl, —$(CH_2)_n$CN, —$(CH_2)_n$NR$^9$R$^{10}$, —C(O)O($C_1-C_6$alkyl), —$(CH_2)_nO(C_1-C_6$ alkyl), benzyloxy, phenoxy, phenylthio, —$(CONHSO_2)$R$^{16}$, —CHO, —CF$_3$, —OCF$_3$, pyridyl, amino, amidino, halo, carbamyl, carboxyl, carbalkoxy, —$(CH_2)_nCO_2$H, cyano, cyanoguanidinyl, guanidino, hydrazide, hydrazino, hydrazido, hydroxy, hydroxyamino, nitro, phosphono, —SO$_3$H, thioacetal, thiocarbonyl, furyl, thiophenyl —COR$^9$, —CONR$^9$R$^{16}$, —NR$^9$R$^{10}$, —NCHCOR$^9$, —SO$_2$R$^9$, —OR$^9$, —SR$^9$, CH$_2$SO$_2$R$^9$, tetrazolyl; tetrazolyl substituted with —$(C_1-C_6)$alkyl, phenyl or —$(C_1-C_4)$alkylphenyl; —$(CH_2)_n$OSi$(C_1-C_6)_3$alkyl and $(C_1-C_6)$alkylcarbonyl; where R$^9$ and R$^{10}$ are independently hydrogen, —CF$_3$, phenyl, —$(C_1-C_4)$alkyl, or —$(C_1-C_4)$alkylphenyl, where n is from 1 to 8, where R$^{15}$ is —$(C_1-C_6)$alkyl, —CF$_3$, naphthyl or —$(CH_2)_s$phenyl, and where s is from 0 to 5.

A preferred group of non-interfering substituents include hydrogen, —$(C_1-C_6)$alkyl, —$(C_2-C_6)$alkenyl, —$(C_2-C_6)$alkynyl, —$(C_3-C_8)$cycloalkyl, —$(C_1-C_6)$alkoxy, halo or —$(C_1-C_4)$alkyl phenyl.

Another preferred group of non-interfering substituents include hydrogen, halo, —$(C_1-C_3)$alkyl, —$(C_3-C_4)$cycloalkyl, —$(C_3-C_4)$cycloalkenyl, —O$(C_1-C_2)$alkyl and —S$(C_1-C_2)$alkyl.

The words, "acid linker" refer to a divalent linking group symbolized as, —(L$_a$)—.

The words, "acid linker length", refer to the number of atoms (excluding hydrogen) in the shortest chain of the linking group —(La)— that connects the 7 or 8 position of the tricyclic nucleus with the remainder of the chain. The presence of a carbocyclic ring in —(La)— counts as the number of atoms approximately equivalent to the calculated diameter of the carbocyclic ring. Thus, a benzene or cyclohexane ring in the acid linker counts as 2 atoms in calculating the length of —(La)—. Illustrative acid linker groups are;

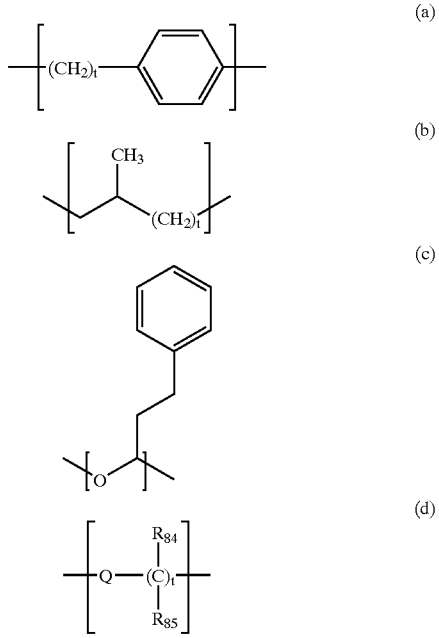

where t is 1 to 5, Q is selected from the group —(CH$_2$)—, —O—, —NH—, and —S—, and R$_{84}$ and R$_{85}$ are each independently selected from hydrogen, —(C$_1$-C$_{10}$)alkyl, aryl, —(C$_1$-C$_{10}$)alkaryl, —(C$_1$-C$_{10}$)aralkyl, carboxy, carbalkoxy, and halo. When t is one (1), groups (a), (b), and (d) have acid linker lengths of 3, 3, and 2, respectively.

The salts of the above tricyclics are an additional aspect of the invention. In those instances where the compounds of the invention possess acidic functional groups, various salts may be formed which are more water soluble and physiologically suitable than the parent compound. Representative pharmaceutically acceptable salts include but are not limited to the alkali and alkaline earth salts such as lithium, sodium, potassium, calcium, magnesium, aluminum and the like. Sodium salts are preferred. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66:1–19 (1977)).

Compounds of the invention may have chiral centers and exist in optically active forms. R- and S-isomers and racemic mixtures are contemplated by this invention. A particular stereoisomer may be prepared by known methods using stereospecific reactions with starting materials containing asymmetric centers already resolved or, alternatively, by subsequent resolution of mixtures of stereoisomers using known methods.

Prodrugs are derivatives of the compounds of the invention which have chemically or metabolically cleavable groups and become, by solvolysis or under physiological conditions, the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives, such as, esters prepared by reaction of the parent acidic compound with a suitable alcohol, or amides prepared by reaction of the parent acid compound with a suitable amine. Simple aliphatic esters (e.g., methyl, ethyl, propyl, isopropyl, butyl, sec-butyl, tert-butyl) or aromatic esters derived from acidic groups pendent on the compounds of this invention are preferred prodrugs. Other preferred esters include morpholinoethyloxy, diethylglycolamide and diethylaminocarbonylmethoxy. In some cases, it is desirable to prepare double ester type prodrugs such as (acyloxy)alkyl esters or ((alkoxycarbonyl)oxy)alkyl esters.

The term "acid protecting group" is used herein as it is frequently used in synthetic organic chemistry, to refer to a group which will prevent an acid group from participating in a reaction carried out on some other functional group in the molecule, but which can be removed when it is desired to do so. Such groups are discussed by T. W. Greene in chapter 5 of Protective Groups in Organic Synthesis, John Wiley and Sons, New York, 1981, incorporated herein by reference in its entirety.

Examples of acid protecting groups include ester or amide derivatives of the acid group, such as, methyl, methoxymethyl, methyl-thiomethyl, tetrahydropyranyl, methoxyethoxymethyl, benzyloxymethyl, phenyl, aryl, ethyl, 2,2,2-trichloroethyl, 2-methylthioethyl, t-butyl, cyclopentyl, triphenylmethyl, diphenylmethyl, benzyl, trimethylsilyl, N,N-dimethyl, pyrrolidinyl, piperidinyl, or o-nitroanilide. A preferred acid-protecting group is methyl.

PREFERRED COMPOUNDS OF THE INVENTION

Preferred Subgroups of Compounds

A preferred subclass of compounds of formula (I) are those wherein R$^{4'}$, is selected from the group consisting of cycloalkyl, cycloalkenyl, phenyl, naphthyl, norbornanyl, bicycloheptadienyl, tolulyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

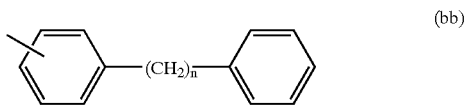

where n is a number from 1 to 8.

Particularly preferred are compounds wherein R$^{4'}$ is selected from the group consisting of

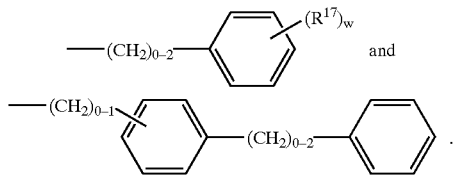

where R17 is a radical independently selected from halo, —($C_1$–$C_{10}$)alkyl, —($C_1$–$C_{10}$)alkoxy, —S—($C_1$–$C_{10}$ alkyl), and —($C_1$–$C_{10}$)haloalkyl, and w is a number from 0 to 5.

Another preferred subclass of compounds of Formula (I) are those wherein A is a substituent having an acid linker with an acid linker length of 2 or 3 and the acid linker group, —($L_a$)—, for A is selected from a group represented by the formula;

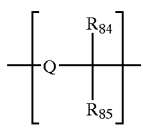

where Q is selected from the group —($CH_2$)—, —O—, —NH—, and —S—, and $R_{84}$ and $R_{85}$ are each independently selected from hydrogen, —($C_1$–$C_{10}$)alkyl, aryl, —($C_1$–$C_{10}$)alkylaryl, —aryl($C_1$–$C_{10}$)alkyl, carboxy, carbalkoxy, and halo.

Most preferred are compounds where the acid linker, —($L_a$)—, for A is selected from the specific groups;

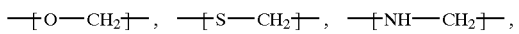

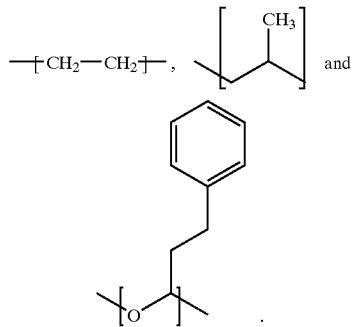

Another preferred subclass of compounds of formula (I) are those wherein A is a substituent having an acid linker with an acid linker length of 3 to 8 atoms and the acid linker group, —($L_a$)—, for A is selected from;

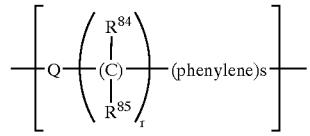

where r is a number from 1 to 7, s is 0 or 1, and Q is selected from the group —($CH_2$)—, —O—, —NH—, and —S—, and $R_{84}$ and $R_{85}$ are each independently selected from hydrogen, —($C_1$–$C_{10}$)alkyl, aryl, —($C_1$–$C_{10}$)alkylaryl, -aryl($C_1$–$C_{10}$)alkyl, carboxy, carbalkoxy, and halo.

Another preferred subclass are compounds where the acid linker, —($L_a$)—, for A is selected from the specific groups;

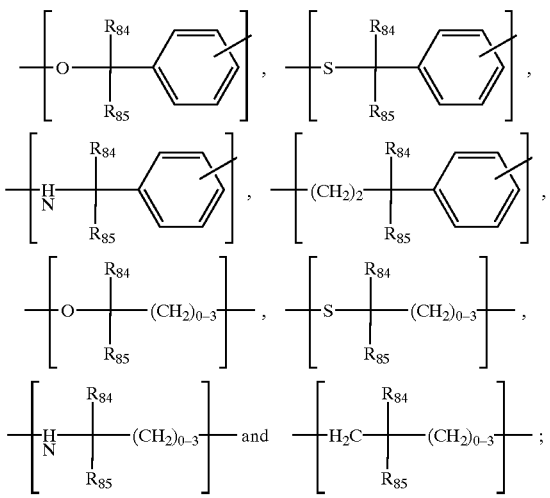

wherein $R_{84}$ and $R_{85}$ are each independently selected from hydrogen, —($C_1$–$C_{10}$)alkyl, aryl, —($C_1$–$C_{10}$)alkaryl, —($C_1$–$C_{10}$)aralkyl, carboxy, carbalkoxy, and halo.

Another preferred group of non-interfering substituents include hydrogen, —O($C_1$–$C_4$)alkyl, halo, —($C_1$–$C_6$)alkyl, phenyl, —($C_1$–$C_4$)alkylphenyl; phenyl substituted with —($C_1$–$C_6$)alkyl, halo, or —$CF_3$; —$CH_2OSi(C_1$–$C_6)_3$alkyl, furyl, thiophenyl, —($C_1$–$C_6$)hydroxyalkyl; or —($CH_2$)$_n R^8$ where $R^8$ is hydrogen, —$CONH_2$, —$NR^9 R^{10}$, —CN or phenyl; where $R^9$ and $R^{10}$ are independently —($C_1$–$C_4$)calkyl or -phenyl($C_1$–$C_4$)alkyl and where n is 1 to 8.

Preferred compounds of the invention are those having the general formula (II)

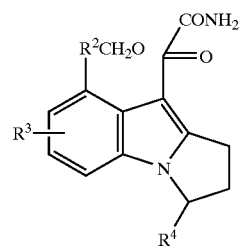
(II)

wherein;

$R^2$ is —$CO_2H$, —$CO_2(C_1$–$C_4$ alkyl);

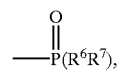

tetrazolyl, —$CONR^9 R^{10}$; —$SO_2 R^{15}$, —$CONHSO_2 R^{15}$ or phenyl substituted with —$CO_2H$ or —$CO_2(C_1$–$C_4$) alkyl, where $R^6$ and $R^7$ are each independently —OH or —O($C_1$–$C_4$)alkyl, $R^9$ and $R^{10}$ are each independently hydrogen, —$CF_3$, —($C_1$–$C_4$)alkyl, phenyl or —($C_1$–$C_4$)alkylphenyl and $R^{15}$ is hydrogen, aryl, —($C_1$–$C_6$)alkyl or —$CF_3$;

$R^3$ is hydrogen, —O($C_1$–$C_4$)alkyl, halo, —($C_1$–$C_6$)alkyl, phenyl, —($C_1$–$C_4$)alkylphenyl; phenyl substituted with —($C_1$–$C_6$)alkyl, halo, or —$CF_3$; —$CH_2OSi(C_1$–$C_6$)$_3$alkyl, furyl, thiophenyl, —($C_1$–$C_6$)hydroxyalkyl, —($C_1$–$C_6$)alkoxy($C_1$–$C_6$)alkyl, —($C_1$–$C_6$)alkoxy($CC_1$–$C_6$)alkenyl, —($C_1$–$C_6$)alkoxy($C_1$–$C_6$)alkyl, —$(C_1-C_6)$alkoxy, —$(C_1-C_6)$alkenyl, or —$(CH_2)_nR^6$, where $R^8$ is hydrogen, —$CONH_2$, —$NR^9R^{10}$, —CN or phenyl, where $R^9$ and $R^{10}$ are independently hydrogen, —$CF_3$, phenyl, —$(C_1-C_4)$alkyl or —$(C_1-C_4)$alkylphenyl and n is 1 to 8; and $R^4$ is —$(C_5-C_{14})$alkyl, —$(C_3-C_{14})$cycloalkyl, pyridyl, phenyl or phenyl substituted with —$(C_1-C_6)$alkyl, halo, —$CF_3$, —$OCF_3$, —$(C_1-C_4)$alkoxy, —CN, —$(C_1-C_4)$alkylthio, phenyl$(C_1-C_4)$alkyl, —$(C_1-C_4)$alkylphenyl, phenyl, phenoxy or naphthyl;

or a pharmaceutically acceptable racemate, solvate, optical isomer, prodrug derivative or salt, thereof.

Preferred Substituents of Compounds of Formula I and II Include the Following:

(a) $R^1$ is —$NH_2$;
(b) $R^2$ is —$CO_2H$ or —$CO_2(C_1-C_4)$alkyl;
(c) $R^2$ is —$NH_2$ or $NR^9R^{10}$ where $R^9$ and $R^{10}$ are hydrogen, —$(C_1-C_4)$alkyl or phenyl $(C_1-C_4)$alkyl;
(d) $R^2$ is phenyl substituted with —$CO_2H$ or —$CO_2(C_1-C_4$ alkyl);
(e) $R^2$ is

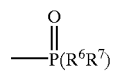

where $R^6$ and $R^7$ are —$O(C_1-C_4$ alkyl), or when one of $R^6$ and $R^7$ is —$O(C_1-C4$ alkyl), the other is —OH;

(f) $R^3$ is hydrogen, —$O(C_1-C4$ alkyl) or —$(CH_2)_nR^8$ where n=2 and $R^8$ is hydrogen or phenyl;
(g) $R^3$ is hydrogen or —$O(C_1-C_4$ alkyl);
(h) $R^3$ is —$(CH_2)_nR^8$ where $R^8$ is —$NR^9R^{10}$,

or —CN, where $R^9$ and $R^{10}$ are —$(C_1-C_4)$alkyl;
(i) $R^3$ is hydrogen, —$O(C_1-C_4)$alkyl, halo, —$(C_1-C_6)$ alkyl, phenyl, —$(C_1-C_4)$alkylphenyl; phenyl substituted with —$(C_1-C_6)$alkyl, halo, or —$CF_3$; —$CH_2OSi(C_1-C_6)$:$_3$alkyl, furyl, thiophenyl, —$(C_1-C_6)$ hydroxyalkyl; or —$(CH_2)_nR^8$ where, where $R^8$ is hydrogen, —$CONH_2$, —$NR^9R^{10}$, —CN or phenyl where $R^9$ and $R^{10}$ are independently hydrogen, —$CF_3$, —$(C_1-C_4)$alkyl or —$(C_1-C_4)$alkylphenyl and n is 1 to 8;
(j) $R^4$ is phenyl;
(k) $R^4$ is phenyl substituted at the 2- and 6-position of the phenyl ring with —$(C_1-C_4)$alkyl, $(C_1-C_4)$alkoxy, halo or phenyl;
(l) $R^4$ is phenyl substituted at the 2- or 6-position of the phenyl ring with —$(C_1-C_4)$alkyl, —$(C_1-C_4)$alkoxy, halo or phenyl;
(m) $R^4$ is phenyl substituted at the 3- or 5-position of the phenyl ring with —$(C_1-C_4)$alkyl, —$(C_1-C_4)$alkoxy, halo or phenyl;
(n) $R^4$ is —$(C_6-C_{14})$alkyl);
(o) A is —$OCH_2$—;
(p) Z is —C=O;
(q) when A is attached to the remainder of the ring at the 8-position, f is 1; and
(r) when A is attached to the remainder of the ring at the 7-position, f is 3.

Some typical compounds of this invention are provided in Table 1 below, however, such named compounds are not intended to limit the scope of this invention in any way.

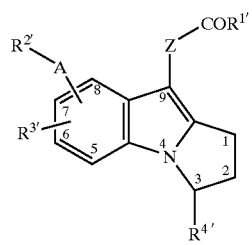

| $R^{1'}$ | $R^{2'}$ | $R^{3'}$ | $R^{4'}$ | A | Z |
|---|---|---|---|---|---|
| —$NHNH_2$ | —$CO_2H$ | —H | -c-$(C_3H_5)$ | 8-$O(CH_2)$— | —C(O)— |
| —$NH_2$ | —$CO_2(CH_3)$ | 6-$CH_3$ | -Ph | 8-$SCH_2$— | —$CH_2$— |
| —$NH_2$ | —$CO_2(CH_2CH_3)$ | —H | -c-$(C_6H_{11})$ | 8-$O(CH_2)$— | —$CH_2$— |
| —$NH_2$ | —$CO_2(CH_2CH_2CH_3)$ | 5-$CH_2Ph$ | -Ph | 8-$(CH_2)_2$— | —C(O)— |
| —$NH_2$ | —$CO_2(CH_3)$ | —H | -Ph-o-Cl | 7-$O(CH_2)_3$ | —C(O)— |
| —$NH_2$ | —$CO_2(CH_2CH_3)$ | —H | -Ph-p-$CF_3$ | 8-$O(CH_2)$— | —$CH_2$— |
| —$NH_2$ | —$CON(CH_3)_2$ | —H | -Ph | 8-$NHCH_2$— | —C(O)— |
| —$NH_2$ | —$CO_2H$ | 6-$OCH_3$ | -pyridyl | 8-$(CH_2)_2$— | —$CH_2$— |
| —$NHNH_2$ | —$CO_2(CH_2CH_2CH_3)$ | —H | -Ph-o-CN | 8-$O(CH_2)$— | —$CH_2$— |
| —$NH_2$ | —$CONH(CH_3)$ | —H | -Ph-p-Br | 7-$O(CH_2)_2$— | —C(O)— |
| —$NH_2$ | —$CO_2H$ | 5-$CH_2CH_3$ | -Ph | 7-$S(CH_2)_3$— | —C(O)— |
| —$NH_2$ | —$PO_3H_2$ | —H | -c-$(C_3H_5)$ | 8-$SCH_2$— | —C(O)— |
| —$NH_2$ | —$CO_2(CH_2CH_3)$ | —H | -Ph-o-$OCH_2CH_3$ | 8-$O(CH_2)$— | —$CH_2$— |
| —$NH_2$ | —$CO_2H$ | 5-$CH_2CH_2CH_3$ | -Ph-m-$CH_3$ | 7-$O(CH_2)_3$ | —C(O)— |
| —$NH_2$ | $CONH_2$ | —H | -c-$(C_5H_9)$ | 8-$SCH_2$— | —C(O)— |
| —$NH_2$ | —$CO_2(CH_3)$ | 5-$OCH_2CH_3$ | -Ph-o-$CF_3$ | 8-$(CH_2)_2$— | —C(O)— |
| —$NH_2$ | —$PO_3H_2$ | 6-$CH_2CH_2CH_3$ | -Ph | 8-$O(CH_2)$— | —$CH_2$— |

(I)

| R[1'] | R[2'] | R[3'] | R[4'] | A | Z |
|---|---|---|---|---|---|
| —NHNH$_2$ | —P(O)(OCH$_3$)$_2$ | —H | -Ph-m-OCH$_3$ | 8-S(CH$_2$)$_2$— | —CH$_2$— |
| —NH$_2$ | —CO$_2$H | 6-CH$_2$Ph | -Ph-o-CN | 8-O(CH$_2$)— | —C(O)— |
| —NH$_2$ | —P(O)(OH)(OCH$_3$) | —H | -Ph-p-Br | 8-NH(CH$_2$)$_2$— | —CH$_2$— |
| —NH$_2$ | —CO$_2$(CH$_3$) | 5-CH$_2$CH$_3$ | -Ph | 8-O(CH$_2$)— | —CH$_2$— |
| —NH$_2$ | CONH$_2$ | —H | -Ph-m-CH$_3$ | 7-S(CH$_2$)$_3$— | —CH$_2$— |
| —NH$_2$ | —CO$_2$(CH$_2$CH$_2$CH$_3$) | 5-Ph | -Ph | 7-(CH$_2$)$_3$— | —C(O)— |
| —NH$_2$ | —P(O)(OH)(OCH$_3$) | —H | -c-(C$_3$H$_5$) | 8-SCH$_2$— | —C(O)— |
| —NH$_2$ | —CO$_2$H | 5-CH$_2$CH$_2$Ph | -pyridyl | 7-S(CH$_2$)$_3$— | —CH$_2$— |
| —NH$_2$ | —CO$_2$(CH$_3$) | 5-CH$_2$CH$_2$Ph | -Ph | 7-NH(CH$_2$)$_2$— | —CH$_2$— |
| —NH$_2$ | —P(O)(OCH$_3$)$_2$ | —H | -Ph-o-OCH$_2$CH$_3$ | 8-SCH$_2$— | —C(O)— |
| —NH$_2$ | —CO$_2$H | 5-OCH$_2$CH$_3$ | -Ph | 7-O(CH$_2$)$_3$ | —CH$_2$— |
| —NH$_2$ | —CON(CH$_3$)$_2$ | —H | -Ph-m-OCH$_3$ | 7-(CH$_2$)$_3$— | —CH$_2$— |
| —NHNH$_2$ | —CO$_2$(CH$_2$CH$_3$) | —H | -c-(C$_5$H$_9$) | 8-SCH$_2$— | —C(O)— |
| —NH$_2$ | —CO$_2$(CH$_3$) | 5-Ph | -Ph | 7-S(CH$_2$)$_3$— | —C(O)— |

Key:

"c" means cyclic
"o" means ortho
"m" means meta
"p" means para

For A and R$^3$ the numerical prefix corresponds to the position the substituent is attached to the tricyclic ring

Synthesis Methods

Compounds of the invention can be prepared, generally, as described in Scheme I. Unless otherwise specified, all reactions are preferably run under an inert atmosphere such as nitrogen. The reactions may be monitored for completion by ordinary methods such as by thin layer chromatography. Unless otherwise specified, the reactions may be conducted using any solvent which is inert to the reactants and has adequate solvency for them.

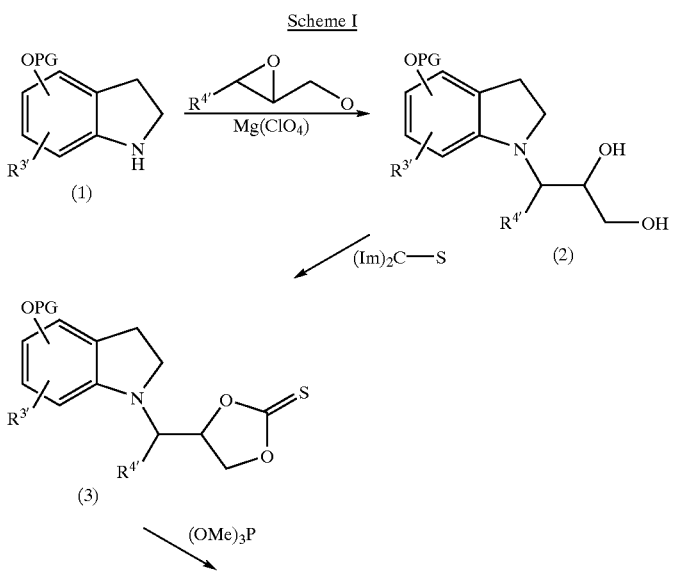

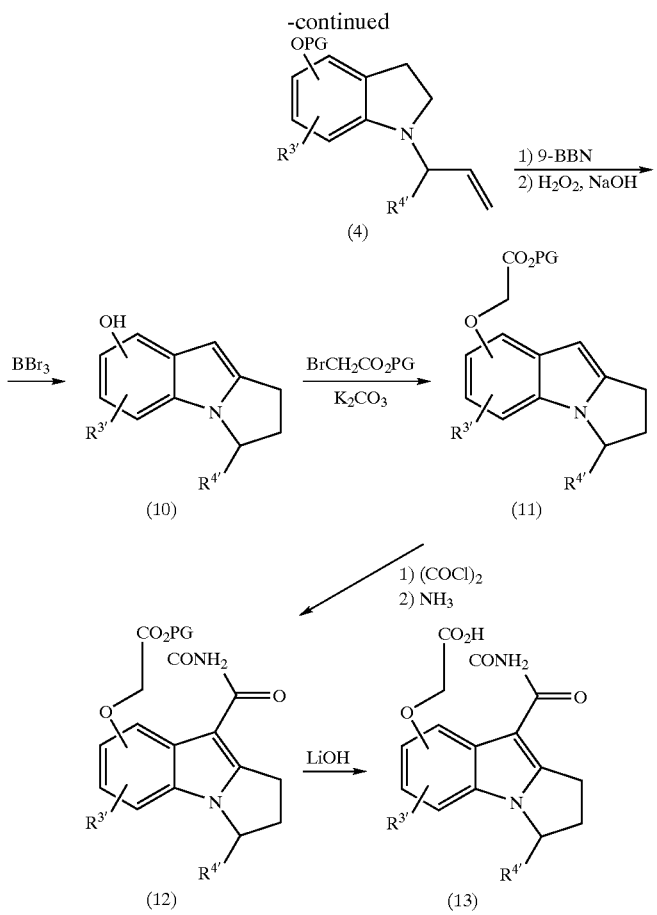

PG = oxyprotecting group;
methyl, benzyl, isopropyl, allyl

In a Lewis acid mediated acylation, starting material (1) is treated with a slight molar excess of a weak acid, preferably magnesium perchlorate, then reacted with an appropriately substituted glycidic where $R^4$ is preferably phenyl. The reaction is preferably conducted in an aprotic solvent, preferably acetonitrile, at temperatures of from about 0° C. to 50° C. The arylglycidic alcohols used in this step are readily available as optically pure compounds [Katsuki, T; Sharpless, K. B. J. Am. Chem. Soc., 1980, 102, 5974] and this reaction is highly stereospecific. For example, using the 1S, 2S glycidic alcohol will give a final product having the R configuration at position 3, and using the 1R, 2R, glycidic alcohol will provide the final product having the S configuration at position 3 since this position is inverted by the epoxide opening reaction and unaffected during the course of all subsequent reactions.

Conversion of dialcohol (2) to a suitable leaving group is achieved by refluxing with thiolcarbonyl diimidazole in a suitable aprotic solvent such as tetrahydrofuran(THF).

Reductive elimination of the leaving group of (3) to form olefin (4) is accomplished by heating with a suitable reducing agent such as trimethyl, triethyl or triphenyl phosphite. The reaction is preferably conducted at temperatures of from about 50° to 120° C. for extended periods of time, from about 20 to 24 hours, preferably about 22 hours.

In a two step, one pot reaction, oxidation of (4) is accomplished by treating first with a borane reagent, preferably 9-borobicylo[3.3.1]nonane followed by treatment with hydrogen peroxide in the presence of an excess of a hydroxide base, preferably sodium hydroxide. Lithium hydroxide may also be employed. Reactions maybe run at temperatures of from about −10° C. to 250° C., preferably at about 0° C. Preferably, the reactions are conducted in an aprotic solvent such as THF.

Aromatization of the indole ring may be accomplished by oxidation of (5) with a slight excess, preferably 1.1 equivalents, of 2,3-dichloro-5,6-dicyano-1,4-benzo quinone (DDQ), at temperatures from about 50° to 110° C., preferably at about 70° C. The reaction is substantially complete in about 5 hours.

Conversion of intermediate (6) to the alkylhalide (7) may be achieved by treatment with a reagent of the formula $CX_4$, where X is halo, preferably chlorine, in the presence of an activating agent, preferably triphenylphosphine. The reaction may be conducted at room temperature and requires extended periods of time, up to about 16 hours, for completion.

Free radical cyclization of (7) is generally accomplished by treatment first with a tin hydride reagent such as tributyl tinhydride, in the presence of a free radical initiatior such as 1,1' azobis(cyclohexanecarbonitrile) (ACN) or 2,2'-azobisisobutyronitrile (AIBN) then with additional aliquots of ACN or AIBN added slowly over a period of about five hours. The reaction is substantially complete about one hour after the last addition of ACN or AIBN. The reaction is preferably conducted in an aprotic, high boiling organic solvent such as degassed toluene, at temperatures of about 110° C.

Oxidation of indoline (8) to indole (9) is accomplished as described above, by oxidation with an oxidizing reagent such as DDQ. Other oxidizing agents are also suitable, however if DDQ is utilized, it is critical that a slight excess (about 1:1 equivalents) is employed. The reaction is preferably conducted in an organic solvent such as dioxane, usually under moderate reaction conditions.

Deprotection of the oxy group of (9) is readily accomplished by treatment with an excess of from about 2 to 10 equivalents of boron tribromide. Other suitable deprotecting reagents include, but are not limited to, pyridine hydrochloride, aluminum chloride, ethane thiol and sodium ethane thiolate. Generally, the reaction is run at low temperatures, preferably in the range of from about $-10°$ C. to ambient temperature in an inert solvent such as methylene chloride.

Alkylation of the hydroxy group is accomplished by treatment with an alkylating agent of the formula $XCH_2R^{2'}$ (where X is halo and $R^{2'}$ is preferably —$CO_2R^5$, —$SO_2R^5$, —$P(O)(OR^5)_2$, or —$P(O)(OR^5)H$, where $R^5$ is an acid protecting group or a prodrug function) in the presence of a base. Preferable, an excess of from about 1.1 to 3 equivalents of alkylating agent is employed and from 1 to 4 equivalents of base. Suitable bases include, but are not limited to, cesium carbonate, potassium carbonate, sodium carbonate, lithium carbonate, sodium bicarbonate, potassium bicarbonate, potassium hydroxide, sodium hydroxide, sodium hydride, potassium hydride and lithium hydride.

The reaction is preferably carried out in an organic solvent such is dimethyl formamide or acetone, however other suitable non reactive solvents may be employed. Generally the reaction is run at ambient temperatures.

Acylation and animation of (11) is accomplished by treatment first with oxaly chloride in an alkyl halide solvent, such as chloroform, followed by treatment with ammonia in the form of a gas or an ammonium salt such as ammonium hydroxide. Suitable solvents include protic polar solvents such as ethanol, methanol, dioxane and water. The reaction is preferably conducted at temperatures of from about 20 to 100° C. Reduction of the carbonyl can be accomplished catalytically or with hydrides.

The acid may be optionally salified, if desired When A is other than oxygen, compounds of the invention can be prepared as described above, using an appropriately substituted indole as the starting material. See also Dillard, et. al., "Indole Inhibitors of Human Non-Pancreatic Secretory Phosphilapase $A_2$2-Indole-3-Acetamides with Additional Functionality", *Journal of Medicinal Chemistry*, Vol. 39, No. 26, pp5137–5158, for preparation of compounds where A is other than oxygen and Z is other than carbonyl.

The following preparations of intermediates and examples of final products futher illustrate the preparation of the compounds of this invention. The examples are illustrative only and are not intended to limit the scope of the invention in any way.

| Abreviations | |
|---|---|
| EtOAc | Ethylacetate |
| 9-BBN | 9-borobicyclo[3.3.1]nonane |
| DDQ | 2,3-dichloro-5,6-dicyano-1,4-benzoquinone |
| ACN | 1,1'azobis(cyclohexanecabonitrile) |
| AIBN | 2,2'-azobisisobutyronitrile |

| -continued | |
|---|---|
| Abreviations | |
| $Et_2O$ | Diethylether |
| DMF | Dimethylformamide |
| MeOH | Methanol |
| THF | Tetrahydrofuran |
| TLC | thin layer chromotography |

EXAMPLE I

2-[1-H-2,2-Dihydro-1-(2-amine-1,2-dioxoethyl)-3-phenyl-pyrrolo[1,2-a]indol-8-yl]oxyacetic Acid

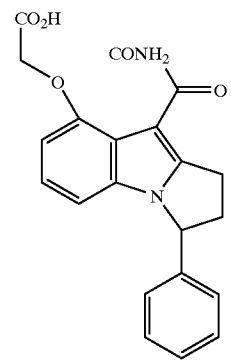

A. Preparation of 2-Hydroxy-3-(4-methoxyindolin-1-yl)-3-phenylpropanol

A solution of 1.00 g (6.62 mmol) of 4-methoxyindoline (Gangjee et al., *J. Med. Chem.* 1997, 40, 479–485) and 1.90 g (8.51 mmol) of magnesium perchlorate in 20 mL of $CH_3CN$ was treated in a dropwise manner with a solution of 1.00 g (6.62 mmol) of 2,3-epoxy-3-phenyl-1-propanol (Ogata and Tomizawa, *Bull. Chim. Soc. Jap.* 1977, 50, 261–265) in 10 mL of $CH_3CN$. The reaction was stirred at ambient temperature for 2.5 hours and was diluted with 30 mL of saturated aqueous $NaHCO_3$. The organic layer was separated and the aqueous phase was extracted with EtOAc (2×20 mL). The combined organic layers were dried ($Na_2SO_4$), filtered, and concentrated in vacuo. The oil was purified by radial chromatography ($SiO_2$; 10% then 20% then 30% EtOAc in hexanes) to afford 1.55 g (5.17 mmol; 78%) of the subtitled compound as a solid.

IR ($CHCl_3$) 1623, 1483, 1467, 1255, 1088 $cm^{-1}$; FDMS 300 (M+1); Elemental Analysis for $C_{18}H_{21}NO_3$: Calculated: C, 72.22; H, 7.07; N, 4.68. Found: C, 72.37; H, 7.09; N, 4.73.

B. Preparation of 4-[ -(4-methoxyindolin-1-yl)] phenylmethyl-1,3-dioxolene-2-thione A solution of 23.0 g (76.8 mmol) of the compoud of Part A and 1.00 g (8.19 mmol) of dimethylaminopyridine in 350 mL of THE was treated with 16.9 g (94.8 mmol) of 1,1'-thiocarbonyldiimidazole. The mixture was heated to reflux for 1 hour, cooled, diluted with 500 mL of EtOAc and the mixture washed with $H_2O$ (2×200 mL) and brine (200 mL). The organic layer was dried ($Na_2SO_4$), filtered, and concentrated in vacuo. The residue was purified by flash chromatography ($SiO_2$; $CHCl_3$) to afford 15.8 g (46.3 mmol; 60%) of the title compound as a tan solid.

IR ($CHCl_3$) 1613, 1481, 1467, 1298, 1161, 1082, 982 $cm^{-1}$; FDMS 342 (M+1); Elemental Analysis for $C_{19}H_{19}NO_2S$: calculated: C, 66.84; H, 5.61; N, 4.10. Found: C, 66.66; H, 5.79; N, 4.05.

C. Preparation of 3-(4-Methoxyindolin-1-yl)-3-phenylpropene

A solution of 15.6 g (45.7 mmol) the compound of Part B in 200 mL of trimethyl phosphite was heated to 90° C. for 22 hours. The reaction was concentrated in vacuo and the oil was purified by flash chromatography ($SiO_2$; 0% then 1% then 2% EtOAc in hexanes) to afford 10.4 g (39.3 mmol; 86% of the subtitled compound as an oil.

IR ($CHCl_3$) 3007, 1614, 1481, 1467, 1254, 1083, 1039 $cm^{-1}$; FDMS 266 (M+1); Elemental Analysis for $C_{18}H_{19}NO$: Calculated: C, 81.48; H, 7.22; N, 5.28. Found: C, 81.22; H, 7.24; N, 5.27.

D. Preparation off 3-(4-Methoxyindolin-1-yl)-3-phenylpropanol

A 0° C. solution of 1.00 g (3.77 mmol) of the compound of Part C in 25 mL of THF was treated with 830 mg (3.81 mmol) of 9-BBN in portions. After complete addition, the cold bath was removed and the reaction stirred at ambient temperature until TLC show ed complete consumption of starting material (3 hours). The reaction was cooled to 0° C. and was quenched with ice. The mixture was treated with 3.60 mL of 2N aqueous NaOH followed by 1.80 ml 30% aqueous $H_2O_2$. The mixture was stirred at 0° C. for 2 hours, solid NaCl was added and the layers separated. The organic layer was dried ($Na_2SO_4$), filtered, and concentrated in vacuo to give an oil. Flash chromatography ($SiO_2$; 0% then 5% then 10% then 15% EtOAc in hexanes) afforded 970 mg (3.42 mmol; 91%) of the subtitled compound as an oil.

IR($CHCl_3$) 3435, 1613, 1482, 1467, 1255, 1084 $cm^{-1}$; FDMS 284 (M+1); Elemental Analysis for $C_{18}H_{21}NO_2$: Calculated: C, 76.30; H, 7.47; N, 4.94. Found: C, 76.36; H, 7.42; N, 5.01.

E. Preparation of 3-(4-Methoxyindol-1-yl)-3-phenylpropanol

A 0° C. solution of 850 mg (3.00 mmol) of the title compound of Part D in 40 mL of dioxane was treated with 750 mg (3.30 mmol) of DDQ. The cold bath was removed and the deep blue reaction stirred at ambient temperature for 1 hour. The reaction was heated at 70° C. for 1 hour, cooled, and concentrated in vacuo. The residue was partitioned between 50 mL of EtOAc and 50 mL of 0.2 N aqueous NaOH. The organic layer was separated, washed with $H_2O$ (50 mL) and brine (50 mL), passed over a bed of $SiO_2$, and concentrated in vacuo to afford 710 mg (2.52 mmol; 84%) of the subtitled compound as a solid.

IR ($CHCl_3$) 3620, 1611, 1580, 1492, 1442, 1255, 1068, 1042 $cm^{-1}$; FDMS 284 (M+1); Elemental Analysis for $C_{18}H_{19}NO_2$: Calculated: C, 76.84; H, 6.81; N, 4.98. Found: C, 76.70; H, 6.70; N, 5.08.

F. Preparation of 3-(4-Methoxyindol-1-yl)-3-phenylpropylchloride

A slurry of 3.00 (10.7 mmol) of the compound of part G and 8.30 g (31.6 mmol) of triphenyl phosphine in 150 mL of $CCl_4$ was heated to 60° C. for 16 hours. The reaction was cooled, filtered, and concentrated in vacuo. The residue was purified by flash chromatography ($SiO_2$; 0% to 1% to 2% to 3%, EtOAc in hexanes) afforded 2.89 g (9.64 mmol; 90%) of the subtitled compound as an oil.

IR ($CHCl_3$) 3007, 1612, 1582, 1492, 1442, 1255, 1068 $cm^{-1}$; FDMS 300 (M+1); Elemental Analysis for $C_{18}H_{18}ClNO$: Calculated: C, 72.11; H, 6.05; N, 4.67. Found: C, 71.97; H, 5.91; N, 4.76.

G. Preparation of 1-H-2,3,9,9a-Tetrahydro-8-methoxy-3-phenylpyrollo[1,2-a]indole A solution of 2.55 g (8.51 mmol) of the compound of part F, 2.90 mL (10.78 mmol) of $Bu_3SnH$, and 115 mg (0.47 mmol) of ACN in 400 mL of toluene was degassed and was heated to a mild reflux. A solution of 115 mg (0.70 mmol) of AIBN in 60 mL of toluene was added dropwise over 5 hours. After an additional 1 hour of reflux, the reaction was concentrated in vacuo. The residue was taken up in 400 mL of $Et_2O$ and the solution treated with 200 mL of 25% (w/v) aqueous KF. The mixture was stirred vigorously for 4 hours, filtered, and the layers separated. The organic layer was dried ($Na_2SO_4$), filtered and concentrated in vacuo. The oil was purified by flash chromatography ($SiO_2$; 0% to 0.5% to 1% EtOAc in hexanes). The fractions containing the desired product were combined and concentrated in vacuo to give 1.34 g of a white solid. Recrystallization from $CH_3CN$ afforded 1.21 g (4.56 mmol; 54%) of the subtitled compound as a white solid.

IR ($CHCl_3$) 2963, 2937, 1602, 1487, 1467, 1441, 1362, 1251, 1124, 1076 $cm^{-1}$; FDMS 266 (M+1); Elemental Analysis for $C_{18}H_{19}NO$: Calculated: C, 81.48; H, 7.22; N, 5.28. Found: C, 81.40; H, 7.23; N, 5.34.

H. Preparation of 1-H-2,3-dihydro-8-methoxy-3-phenylpyrrolo[1,2-a]indole

A solution of 50 mg (0.19 mmol) of the compound of part G in 3 mL of dioxane was treated with 50 mg (0.22 mmol) of DDQ. The reaction was stirred at ambient temperature for 1 hour, diluted with 10 mL of $H_2O$, and the mixture extracted with EtOAc (2×10 mL). The combined organic layers were dried ($Na_2SO_4$), filtered, and concentrated in vacuo to give 110 mg of a brown solid. Radial chromatography ($SiO_2$; 1% EtOAc in hexanes) afforded 34 mg (0.13 mmol; 68%) of the subtitled compound as a white solid.

IR ($CHCl_3$) 3006, 1578, 1552, 1498, 1440, 1250, 1082 $cm^{-1}$; FDMS 264 (M+1); Elemental Analysis for $C_{18}H_{17}NO$: Calculated: C, 82.10; H, 6.51; N, 5.32. Found: C, 81.98; H, 6.40; N, 5.60.

I. Preparation of 1-H-2,3-dihydro-4-hydroxy-3-phenylpyrrolo[1,2-a]indole

A solution of 40 mg (0.15 mmol) of the compound of part H in 1 mL of $CH_2Cl_2$ was treated with 0.60 mL of $BBr_3$ (0.60 mmol; 1M in $CH_2Cl_2$). The reaction was stirred at ambient temperature until TLC analysis showed complete consumption of starting material (2 hours). The reaction was cooled to 0° C. and was quenched by the addition of 1 mL of $H_2O$. The mixture was diluted with 5 mL of $CH_2Cl_2$ and 5 mL of $H_2O$. The organic layer was separated, dried ($Na_2SO_4$), filtered, and concentrated in vacuo to give a pink solid. Radial chromatography ($SiO_2$; 5% to 10% to 20% EtOAc in hexanes) afforded 35 mg (0.14 mmol; 94%) of the subtitled compound as a white solid.

IR ($CHCl_3$) 3597, 1580, 1553, 1497, 1452, 1255, 1183 $cm^{-1}$; FDMS 250 (M+1); Elemental Analysis for $C_{17}H_{15}NO$: Calculated: C, 81.90; H, 6.06; N, 5.62. Found: C, 81.94; H, 6.02; N, 5.85.

J. Preparation of Methyl 1-H-2,3-dihydro-3-phenylpyrrolo[1,2-a]indol-8-yloxyacetic Acid A mixture of 800 mg (3.21 mmol) of the compound of Part I and 1.31 g (4.02 mmol) of $Cs_2CO_3$ in 20 mL of DMF was cooled to 0° C. and was treated with 0.54 mL (5.70 mmol) of methyl bromoacetate. After complete addition, the cold bath was removed and the reaction stirred at ambient temperature until TLC analysis indicated complete consumption of starting material (6 hours). The reaction was concentrated in vacuo and the residue partitioned between 100 mL of H$_2$O and 100 mL of EtOAc. The organic layer was separated, washed with H$_2$O (100 mL) and brine (100 mL), dried (Na$_2$SO$_4$), filtered, and concentrated in vacuo to give 2.10 g of a solid. Purification by flash chromatography (SiO$_2$; 5% to 10% to 15% EtOAc in hexanes) afforded 990 mg (3.08 mmol; 96%) of the title compound as a white solid.

IR (CHCl$_3$) 1761, 1738, 1498, 1441, 1237, 1179 cm$^{-1}$; FDMS 322 (M+1); Elemental Analysis for C$_{20}$H$_{19}$NO$_3$: Calculated; C, 74.75; H, 5.96; N, 4.36. Found: C, 74.77; H, 5.94; N, 4.59.

K. Preparation of Methyl 2-[1-H-2,3-Dihydro-9-(2-amino-1,2-dioxoethyl)-3-phenylpyrrolo[1,2a]indole 8-yl]Oxyacetic Acid A 0° C. solution of 300 mg (0.93 mmol) of the compound of part j and 0.09 mL (1.10 mmol) of pyridine in 10 mL of CH$_2$Cl$_2$ was treated with 0.09 mL (1.04 mmol) of oxalyl chloride. After complete addition, the cold bath was removed and the reaction stirred at ambient temperature for 40 minutes. Ammonia gas was bubbled into the mixture for 5 minutes, the reaction vessel capped, and the contents stirred for 1 hour. The reaction was diluted with H$_2$O (50 mL) and EtOAc (50 mL). The mixture was filtered to give 270 mg of a solid which was recrystallized from MeOH to afford 260 mg (0.66 mmol; 71%) of the subtitled compound as a white solid.

IR (CHCl$_3$) 3313, 1749, 1681, 1638, 1617, 1510, 1497, 1446, 1424, 1363, 1225, 1134, 702 cm$^{-1}$; FDMS 393 (M+1); Elemental Analysis for C$_{22}$H$_{20}$N$_2$O$_5$: Calculated: C, 67.34; H, 5.14; N, 7.14. Found: C, 67.57; H, 5.01; N, 7.04.

L. Preparation of 2-[1-H-2,3-Dihydro-9-(2-amino-1, 2-dioxoethyl)-3-phenylpyrrolo[1,2-a]indol-8-yl] oxyacetic Acid A slurry of 100 mg (0.25 mmol) of the compound of part K in 1.8 mL of THF and 0.6 mL of MeOH was treated with 0.6 mL of 1 N aqueous LiOH. The reaction mixture turned from a granular slurry to a gelantanous mass after minutes. The mixture was stirred for 14 hours and was concentrated in vacuo. The residue was stirred in 25 mL 0.2 N aqueous NaOH for 1 hour, filtered, and dried to afford 91 mg (0.24 mmol; 96%) of the subtitled compound as a white solid.

IR (CHCl$_3$) 3147, 1760, 1672, 1626, 1611, 1577, 1501, 1492, 1453, 1411, 1347, 1259, 1138, 701 cm$^{-1}$; FDMS 379 (M+1); Elemental Analysis for C$_{21}$H$_{18}$N$_2$O$_5$: Calculated: C, 66.66; H, 4.79; N, 7.40. Found: C, 66.86; H, 5.02; N, 7.16.

The intermediates and final products may be isolated and purified by conventional techniques, for example by concentration of the solvents, followed by washing of the residue with water, then purification by conventional techniques, such as chromatography or recrystallization. It will be readily appreciated by the skilled artisan that the starting materials are either commercially available or can be readily prepared by known techniques from commercially available starting materials. All other reactants used to prepare the compounds in the instant invention are commercially available.

Therapeutic Use of Tricyclic Compounds

The compounds described herein are believed to achieve their beneficial therapeutic action principally by direct inhibition of human sPLA$_2$, and not by acting as antagonists for arachidonic acid, nor other active agents below arachidonic acid in the arachidonic acid cascade, such as 5-lipoxygenases, cyclooxygenases, etc.

The method of the invention for inhibiting sPLA$_2$ mediated release of fatty acids comprises contacting sPLA$_2$ with an therapeutically effective amount of the compound of Formula (I) or its salt.

The compounds of the invention may be used in a method of treating a mammal (e.g., a human) to alleviate the pathological effects of sepsis, septic shock, adult respiratory distress syndrome, pancreatitis, trauma-induced shock, asthma, rheumatoid arthritis, osteoarthritis, acute bronchitis, chronic bronchitis, Inflammatory Bowel Disease, apoptosis, stroke, cystic fibrosis, allergic rhinitis, acute bronchiolitis, chronic bronchiolitis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, Joint ell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint, hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis; and related diseases (preferably, sepsis, septic shock, adult respiratory distress syndrome, pancreatitis, trauma-induced shock, asthma, rheumatoid arthritis, osteoarthritis, acute bronchitis, chronic bronchitis, Inflammatory Bowel Disease) wherein the method comprises administering to the mammal a compound of formula (I) in a therapeutically effective amount. A "therapeutically effective" amount is an amount sufficient to inhibit sPLA$_2$ mediated release of fatty acid and to thereby inhibit or prevent the arachidonic acid cascade and its deleterious products. The therapeutic amount of compound of the invention needed to inhibit sPLA$_2$ may be readily determined by taking a sample of body fluid and assaying it for sPLA$_2$ content by conventional methods.

Throughout this document, the person or animal to be treated will be described as a "mammal", and it will be understood that the most preferred subject is a human. However it must be noted that the study of adverse conditions of the central nervous system in non-human animals is only now beginning, an that some instances of such treatments are coming into use. Accordingly, use of the present compounds in non-human animals is contemplated.

It will be understood that the dosage ranges for other animals will necessarily be quite different from the doses administered to humans, and accordingly that the dosage ranges described be recalculated. For example, a small dog may be only $\frac{1}{10}^{th}$ of a typical human's size, and it will therefore be necessary for a much smaller dose to be used. The determination of an effective amount for a certain non-human animal is carried out in the same manner described below in the case of humans, and veterinarians are well accustomed to such determinations.

Pharmaceutical Formulations of the Invention

As previously noted, the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

In general, the compounds of the invention are most desirably administered at a dose that will generally afford effective results without causing any serious side effects and can be administered either as a single unit dose, or if desired, the dosage may be divided into convenient subunits administered at suitable times throughout the day.

The specific dose of a compound administered according to this invention to obtain therapeutic or prophylactic effects will, of course, be determined by the particular circumstances surrounding the case, including, for example, the route of administration, the age, weight and response of the individual patient, the condition being treated and the severity of the patient's symptoms. Typical daily doses will contain a non-toxic dosage level of from about 0.01 mg/kg to about 50 mg/kg of body weight of an active compound of this invention.

Preferably, the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

A "chronic" condition means a deteriorating condition of slow progress and long continuance. As such, it is treated when it is diagnosed and continued throughout the course of the disease. An "acute" condition is an exacerbation of short course followed by a period of remission. In an acute event, compound is administered at the onset of symptoms and discontinued when the symptoms disappear.

For example, pancreatitis, trauma-induced shock, bronchial asthma, allergic rhinitis and rheumatoid arthritis may occur as an acute event or a chronic event. Thus, the treatment of these conditions contemplates both acute and chronic forms. Septic shock and adult respiratory distress, on the other hand, are acute conditions treated when diagnosed.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the compounds of the invention together with a pharmaceutically acceptable carrier or diluent therefor. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention.

Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula I or II or a pharmaceutically acceptable salt, solvate, or prodrug thereof.

FORMULATION 1

Hard gelatin capsules are prepared using the following ingredients:

|  | Quantity (mg/capsule) |
| --- | --- |
| Compound of Example 1 | 250 |
| Starch, dried | 200 |
| Magnesium stearate | 10 |
| Total | 460 mg |

FORMULATION 2

A tablet is prepared using the ingredients below:

|  | Quantity (mg/tablet) |
|---|---|
| Compound of Example 1 | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

FORMULATION 3

An aerosol solution is prepared containing the following components:

|  | Weight |
|---|---|
| Compound of Example 1 | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

| Compound of Example 1 | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

| Compound of Example 1 | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| Compound of Example 1 | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

| Compound of Example 1 | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| Compound of Example 1 | 100 mg |
|---|---|
| Isotonic saline | 1,000 ml |

The solution of the above ingredients generally is administered intravenously to a subject at a rate of 1 ml per minute.

ASSAY EXPERIMENTS

Assay Example 1

The following chromogenic assay procedure was used to identify and evaluate Inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, Analytical Biochemistry, 204, pp. 190–197, 1992 (the disclosure of which is incorporated herein by reference):

| Reagents: | |
|---|---|
| REACTION BUFFER | |
| $CaCl_2.2H_2O$ | (1.47 g/L) |
| KCl | (7.455 g/L) |
| Bovine Serum Albumin (fatty acid free) (Sigma A-7030, product of Sigma Chemical Co. St. Louis MO, USA) | (1 g/L) |
| TRIS HCl | (3.94 g/L) |
| pH 7.5 (adjust with NaOH) | |
| ENZYME BUFFER | |
| 0.05 $NaOAc.3H_2O$, pH 4.5 | |
| 0.2 NaCl | |
| Adjust pH to 4.5 with acetic acid | |
| DTNB | |
| 5,5'-dithiobis-2-nitrobenzoic acid | |
| RACEMIC DIHEPTANOYL THIO - PC | |
| racemic 1,2-bis(heptanoylthio)-1,2-dideoxy-sn-glycero-3-phosphorylcholine | |
| TRITON X-100 prepare at 6.249 mg/ml in reaction buffer to equal 10 uM | |
| TRITON X-100 is a polyoxy ethylene non-ionic detergent supplied by Pierce Chemical Company, 3747 N. Meridian Road, Rockford, Illinois 61101. | |

Reaction Mixture

A measured volume of racemic diheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains lmM diheptanoly thio-PC substrate, 0.29 mm TRITON X-100 detergent, and 0.12 mm DTMB in a buffered aqueous solution at pH 7.5.

Assay Procedure:
1. Add 0.2 ml reaction mixture to all wells;
2. Add 10 ul test compound (or solvent blank)to appropriate wells, mix 20 seconds;
3. Add 50 nanograms of $sPLA_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, $IC_{50}$ values were determined. Typically, the $IC_{50}$ values were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ were determined by plotting log concentration versus inhibition values in the range from 10–90% inhibition.

Compounds of the instant invention were tested in Assay Example 1 and were found to be effective at concentrations of less than 100 $\mu$M.

Assay Example 2

Method:

Male Hartley strain guinea pigs (500–700 g) were killed by cervical dislocation and their heart and lungs removed intact and placed in aerated (95% $O_2$:5% $CO_2$) Krebs buffer. Dorsal pleural strips (4×1×25 mm) were dissected from intact parenchymal segments (8×4×25 mm) cut parallel to the outer edge of the lower lung lobes. Two adjacent pleural strips, obtained from a single lobe and representing a single tissue sample, were tied at either end and independently attached to a metal support rod. One rod was attached to a Grass force-displacement transducer Model FTO3C, (product of Grass Medical Instruments Co., Quincy, Mass., USA). Changes in isometric tension were displayed on a monitor and thermal recorder (product of Modular Instruments, Malvern, Pa.). All tissues were placed in 10 ml jacketed tissue baths maintained at 37° C. The tissue baths were continuously aerated and contained a modified Krebs solution of the following composition (millimolar) NaCl, 118.2; KCl, 4.6; $CaCl_2.2H_2O$, 2.5; $MgSO_4.7H_2O$, 1.2; $NaHCO_3$, 24.8; $KH_2PO_4$, 1.0; and dextrose, 10.0. Pleural strips from the opposite lobes of the lung were used for paired experiments. Preliminary data generated from tension/response curves demonstrated that resting tension of 800 mg was optimal. The tissues were allowed to equilibrate for 45 min. as the bath fluid was changed periodically.

Cumulative Concentration-response Curves:

Initially tissues were challenged 3 times with KCl (40 mM) to test tissue viability and to obtain a consistent response. After recording the maximal response to KCl, the tissues were washed and allowed to return to baseline before the next challenge. Cumulative concentration-response curves were obtained from pleural strips by increasing the agonist concentration ($sPLA_2$) in the tissue bath by half-$log_{10}$ increments while the previous concentration remained in contact with the tissues (Ref.1, supra.). Agonist concentration was increased after reaching the plateau of the contraction elicited by the preceding concentration. One concentration-response curve was obtained from each tissue. To minimize variability between tissues obtained from different animals, contractile responses were expressed as a percentage of the maximal response obtained with the final KCl challenge. When studying the effects of various drugs on the contractile effects of $sPLA_2$, the compounds and their respective vehicles were added to the tissues 30 minutes prior to starting the $sPLA_2$ concentration-response curves.

Statistical Analysis:

Data from different experiments were pooled and presented as a percentage of the maximal KCl responses (mean±S.E.). To estimate the drug induced rightward shifts in the concentration response curves, the curves were analyzed simultaneously using statistical nonlinear modeling methods similar to those described by Waud (1976), Equation 26, p. 163, (Ref.2). The model includes four parameters: the maximum tissue response which was assumed the same for each curve, the $ED_{50}$ for the control curve, the steepness of the curves, and the $pA_2$, the concentration of antagonist that requires a two-fold increase in agonist to achieve an equivalent response. The Schild slope was determined to be 1, using statistical nonlinear modeling methods similar to those described by Waud (1976), Equation 27, p. 164 (Ref. 2). The Schild slope equal to 1 indicates the model is consistent with the assumptions of a competitive antagonist; therefore, the $pA_2$ may be interpreted as the apparent $K_B$, the dissociation constant of the inhibitor.

To estimate the drug-induced suppression of the maximal responses, $sPLA_2$ responses (10 ug/ml) were determined in the absence and presence of drug, and percent suppression was calculated for each pair of tissues. Compounds of the instant invention were tested in Assay Example 2 and were found to be effective at concentrations below 20 $\mu M$.

Ref. 1—Van, J. M.: Cumulative dose-response curves. II. Technique for the making of dose-response curves in isolated organs and the evaluation of drug parameters. Arch. Int. Pharmacodyn. Ther., 143:299–330, 1963.

Ref. 2—Waud, D.: Analysis of dose-response relationships. in Advances in General and Cellular Pharmacology eds Narahashi, Bianchi 1:145–178, 1976.

While the present invention has been illustrated above by certain specific embodiments, it is not intended that these specific examples should limit the scope of the invention as described in the appended claims.

We claim:

1. A compound of the formula (I)

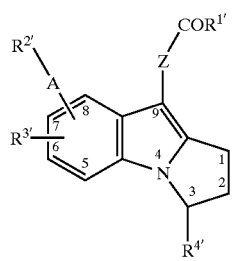
(I)

wherein;

Z is

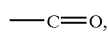

$-CH_2$,

A is $-O(CH_2)_f-$, $-NH(CH_2)_f-$, $-S(CH_2)_f-$, $-(CH_2)_f$ where f is 1 to 3; $-CH=CH-$,

or $-(L_a)-$, wherein $-(L_a)-$ is a linker having a linker length of 1 to 7;

$R^{1'}$ is $-NHNH_2$ or $-NH_2$;
$R^{2'}$ is $-CO_2H$; $-CO_2(C_1-C_4)$alkyl;

where $R^6$ and $R^7$ are each independently $-OH$ or $-O(C_1-C_4)$alkyl; tetrazolyl; $-NR^9R^{10}$ where $R^9$ and $R^{10}$ are independently hydrogen, $-CF_3$, $-(C_1-C_4)$ alkyl, phenyl or $-(C_1-C_4)$alkylphenyl; $-SO_2R^{15}$; $CONHSO_2R^{15}$, where $R^{15}$ is hydrogen, aryl $-(C_1-C_6)$ alkyl or $-CF_3$; or phenyl substituted with $-CO_2H$ or $-CO_2(C_1-C_4)$alkyl;

$R^{3'}$ is selected from non-interfering substituents, carbocyclic radicals, carbocyclic radicals substituted with non-interfering substituents, heterocyclic radicals, and heterocyclic radicals substituted with non-interfering substituents;

$R^{4'}$ is selected from groups (a) and (b) where;
(a) is $-(C_5-C_{20})$alkyl, $-(C_5-C_{20})$alkenyl, $-(C_5-C_{20})$alkynyl, carbocyclic radicals, or heterocyclic radicals, or
(b) is a member of (a) substituted with one or more independently selected non-interfering substituents;

or a pharmaceutically acceptable racemate, solvate, optical isomer, prodrug compound or salt thereof.

2. A compound of the formula (II)

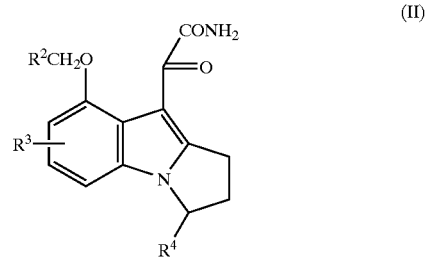
(II)

wherein;

$R^2$ is, $-CO_2H$; $-CO_2(C_1-C_4$ alkyl);

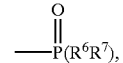

tetrazolyl, $-CONR^9R^{10}$; $-SO_2R^{15}$, $-CONHSO_2R^{15}$, or phenyl substituted with $-CO_2H$ or $-CO_2(C_1-C_4)$alkyl, where $R^6$ and $R^7$ are each independently $-OH$ or $-O(C_1-C_4)$alkyl; $R^9$ and $R^{10}$ are each independently hydrogen, $-CF_3$, $-(C_1-C_4)$ alkyl, phenyl or $-(C_1-C_6)$alkyl and $R^{15}$ is hydrogen, aryl, $-(C_1-C_6)$alkyl or $-CF_3$;

$R^3$ is hydrogen, $-O(C_1-C_4)$alkyl, halo, $-(C_1-C_6)$alkyl, phenyl, $-(C_1-C_4)$alkylphenyl; phenyl substituted with $-(C_1-C_6)$alkyl, halo, or $-CF_3$; $-CH_2OSi(C_1-C_6)$ alkyl, furyl, thiophenyl, $-(C_1-C_6)$hydroxyalkyl, $-(C_1-C_6)$alkoxy$(C_3-C_6)$alkyl, $-(C_3-C_6)$alkoxy $(C_1-C_6)$alkenyl, $-(C_1-C_6)$alkoxy$(C_1-C_6)$alkyl, $-(C_1-C_6)$alkoxy; $-(C_1-C_6)$alkenyl, or $-(CH_2)_nR^8$ where $R^8$ is hydrogen, $-CONH_2$, $-NR^9R^{10}$, $-CN$ or phenyl, where $R^9$ and $R^{10}$ are independently hydrogen, $CF_3$, phenyl, $-(C_1-C_4)$alkyl or $-(C_1-C_4)$alkylphenyl and n is 1 to 8; and $R^4$ is $-(C_5-C_{14})$alkyl, $-(C_3-C_{14})$cycloalkyl, pyridyl, phenyl or phenyl substituted with $-(C_1-C_6)$alkyl, halo, $-CF_3$, $-OCF_3$, $-(C_1-C_4)$alkoxy, $-CN$, $-(C_1-C_4)$alkylthio, phenyl$(C_1-C_4)$alkyl, $-(C_1-C_4)$ alkylphenyl, phenyl, phenoxy or naphthyl;

or a pharmaceutically acceptable racemate, solvate, optical isomer, prodrug compound or salt, thereof.

3. A compound of claim 2 wherein:

A is $-O(CH_2)_f-$ or $-S(CH_2)_f-$;
$R^1$ is $-NH_2$;

$R^2$ is —CO$_2$H; —CO$_2$(C$_1$-C$_4$)alkyl; —CONR$^9$R$^{10}$, where R$^9$ and R$^{10}$ are each independently hydrogen, —CF$_3$, —(C$_1$-C$_4$)alkyl, phenyl or —(C$_1$-C$_4$)alkylphenyl; —P(O)R$^6$R$^7$, where R$^6$ and R$^7$ are each independently —OH or —(C$_1$-C$_4$)alkyl; SO$_2$R$^{15}$ or CONHSO$_2$R$^{15}$, where R$^{15}$ is hydrogen, phenyl or —(C$_1$-C$_4$)alkylphenyl;

R$^3$ is hydrogen, —(C$_1$-C$_6$)alkyl, phenyl or —(C$_1$-C$_4$)alkylphenyl; and R$^4$ is —(C$_3$-C$_{14}$)cycloalkyl, phenyl or phenyl substituted with halo or —(C$_1$-C$_4$)alkoxy;

or a pharmaceutically acceptable racemate, solvate, optical isomer, prodrug compound or salt, thereof.

4. A compound of claim 3 wherein;

$R^2$ is —CO$_2$H; —CO$_2$(C$_1$-C$_4$)alkyl; and $R^4$ is phenyl;

or a pharmaceutically acceptable racemate, solvate, optical isomer, prodrug compound or salt, thereof.

5. A compound of claim 4 which is 2-[1-H-2,3-dihydro-1-(2-amine-1,2-dioxoethyl)-3-phenyl-pyrrolo[1,2-a]indol-3-yl]oxyacetic acid or a pharmaceutically acceptable racemate, solvate, optical isomer, prodrug compound or salt, thereof.

6. A compound of claim 5 which is the S enantiomer.

7. A compound of claim 5 which is the R enantiomer.

8. A compound of any one of claims 1 to 7 wherein the prodrug derivative is a methyl, ethyl, propyl, isopropyl, butyl, morpholinoethyl or diethylglycolamide ester.

9. A pharmaceutical formulation comprising a compound of formula I as claimed in claim 1 together with a pharmaceutically acceptable carrier or diluent therefor.

10. A pharmaceutical formulation comprising a compound of formula II as claimed in claim 2 together with a pharmaceutically acceptable carrier or diluent therefor.

11. A pharmaceutical formulation adapted for the treatment of a condition associated with inhibiting sPLA$_2$, containing a compound of formula I as claimed in claim 1 together with a pharmaceutically acceptable carrier or diluent therefor.

12. A pharmaceutical formulation adapted for the treatment of a condition associated with inhibiting SPLA$_2$, containing a compound of formula II as claimed in claim 2 together with a pharmaceutically acceptable carrier or diluent therefor.

13. A method of selectively inhibiting sPLA$_2$ in a mammal in need of such treatment comprising administering to said mammal a therapeutically effective amount of a compound of formula (I)

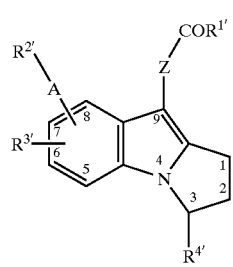

(I)

wherein;

Z is

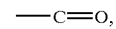

—CH$_2$,

A is —O(CH$_2$)$_f$—; —NH(CH$_2$)$_f$—; —S(CH$_2$)$_f$—; —(CH$_2$)$_f$, where f is 1 to 3; —CH═CH—;

or —(L$_a$)—, where —(L$_a$)— is an acid linker having an acid linker length of 1 to 7;

R$^{1'}$ is —NHNH$_2$ or —NH$_2$;

R$^{2'}$ is —CO$_2$H; —CO$_2$(C$_1$-C$_4$)alkyl;

where R$^6$ and R$^7$ are each independently —OH or —O(C$_1$-C$_4$)alkyl; tetrazolyl; —CONR$^9$R$^{10}$, where R$^9$ and R$^{10}$ are independently hydrogen, —CF$_3$, —(C$_1$-C$_4$)alkyl, phenyl or —(C$_1$-C$_4$)alkylphenyl; —SO$_2$R$^{15}$; —CONHSO$_2$R$^{15}$, where R$^{15}$ is hydrogen, aryl, —(C$_1$-C$_6$)alkyl or —CF$_3$; or phenyl substituted with —CO$_2$H or —CO$_2$(C$_1$-C$_4$)alkyl;

R$^{3'}$ is selected from non-interfering substituents, carbocyclic radicals, carbocyclic radicals substituted with non-interfering substituents, heterocyclic radicals, and heterocyclic radicals substituted with non-interfering substituents;

R$^{4'}$ is selected from groups (a) and (b) where; (a) is —(C$_5$-S$_{20}$)alkyl, —(C$_5$-C$_{20}$)alkenyl, —(C$_5$-C$_{20}$)alkynyl, carbocyclic radicals, or heterocyclic radicals, or (b) is a member of (a) substituted with one or more independently selected non-interfering substituents;

or a pharmaceutically acceptable racemate, solvate, optical isomer, prodrug derivative or salt thereof.

14. A method of selectively inhibiting sPLA$_2$ in a mammal in need of such treatment comprising administering to said mammal a therapeutically effective amount of a compound of formula (II)

(II)

wherein;

R$^2$ is —CO$_2$H, —CO$_2$(C$_1$-C$_4$ alkyl);

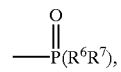

tetrazolyl, —CONR$^9$R$^{10}$; —SO$_2$R$^{15}$, —CONHSO$_2$R$^{15}$, or phenyl substituted with —CO$_2$H or —$CO_2(C_1-C_4)$alkyl, where $R^6$ and $R^7$ are each independently —OH or —$O(C_1-C_4)$alkyl, $R^9$ and $R^{10}$ are each independently hydrogen, —$CF_3$, —$(C_1-C_4)$alkyl, phenyl or —$(C_1-C_4)$alkylphenyl and $R^{15}$ is hydrogen, aryl, —$(C_1-C_6)$alkyl or —$CF_3$;

$R^3$ is hydrogen, —$O(C_1-C_4)$alkyl, halo, —$(C_1-C_6)$alkyl, phenyl, —$(C_1-C_4)$alkylphenyl; phenyl substituted with —$(C_1-C_6)$alkyl, halo, or —$CF_3$; —$CH_2OSi(C_1-C_6)_3$alkyl, furyl, thiophenyl, —$(C_1-C_6)$hydroxyalkyl, —$(C_{114} C_6)$alkoxy$(C_1-C_6)$alkyl, —$(C_1-C_6)$alkoxy$(C_1-C_6)$alkenyl, —$(C_1-C_6)$alkoxy $(C_1-C_6)$alkyl, —$(C_1-C_6)$alkoxy, —$(C_1-C_6)$alkenyl, or —$(CH_2)_n R^8$, where $R^8$ is hydrogen, —$CONH_2$, —$NR^9R^{10}$, —CN or phenyl, where $R^9$ and $R^{10}$ are independently hydrogen, —$CF_3$, phenyl, —$(C_1-C_4)$alkyl or —$(C_{114} C_4)$alkylphenyl and n is 1 to 8; and $R^4$ is —$(C_5-C_{14})$alkyl, —$(C_3-C_{14})$ cycloalkyl, pyridyl, phenyl or phenyl substituted with —$(C_1-C_6)$alkyl, halo, —$CF_3$, —$OCF_3$, —$(C_1-C_4)$alkoxy, —CN, —$(C_1-C_4)$alkylthio, phenyl $(C_1-C_4)$alkyl, —$(C_1-C_4)$alkylphenyl, phenyl, phenoxy or naphthyl;

or a pharmaceutically acceptable racemate, solvate, optical isomer, prodrug derivative or salt, thereof.

15. A method of any one of claims 13 to 14 wherein the mammal is a human.

16. A method of alleviating the pathological effects of sPLA$_2$ related diseases which comprises administering to a mammal in need of such treatment a compound of formula I as claimed in claim 1 in an amount sufficient to inhibit or prevent the arachidonic acid cascade.

17. A method of alleviating the pathological effects of sPLA$_2$ related diseases which comprises administering to a mammal in need of such treatment a compound of formula II as claimed in claim 2 in an amount sufficient to inhibit sPLA$_2$ mediated release of fatty acid.

18. A method of treating a condition selected from the group consisting of sepsis, septic shock, adult respiratory distress syndrome, pancreatitis, trauma-induced shock, asthma, rheumatoid arthritis, osteoarthritis, acute bronchitis, chronic bronchitis, Inflammatory Bowel Disease, apoptosis, stroke, cystic fibrosis, allergic rhinitis, acute bronchiolitis, chronic bronchiolitis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a subject in need of such treatment, a therapeutically effective amount of a compound of formula I (I)

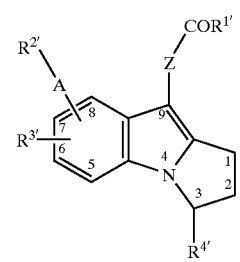

wherein;

Z is

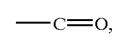

—$CH_2$,

A is —$O(CH_2)_f$—; —$NH(CH_2)_f$—; —$S(CH_2)_f$—; —$(CH_2)_f$, where f is 1 to 3; —CH=CH—;

or —$(L_a)$—, where —$(L_a)$— is an acid linker having an acid linker length of 1 to 7;

$R^{1'}$ is —$NHNH_2$ or —$NH_2$;

$R^{2'}$ is —$CO_2H$; —$CO_2(C_1-C_4)$alkyl;

where $R^6$ and $R^7$ are each independently —OH or —$O(C_1-C_4)$alkyl; tetrazolyl; —$CONR^9R^{10}$, where $R^9$ and $R^{10}$ are independently hydrogen, —$CF_3$, —$(C_2-C_4)$alkyl, phenyl or —$(C_1-C_4)$alkylphenyl; —$SO_2R^{15}$; —$CONHSO_2R^{15}$, where $R^{15}$ is hydrogen, aryl, —$(C_1-C_6)$alkyl or —$CF_3$; or phenyl substituted with —$CO_2H$ or —$CO_2(C_1-C_4)$alkyl;

$R^{3'}$ is selected from non-interfering substituents, carbocyclic radicals, carbocyclic radicals substituted with non-interfering substituents, heterocyclic radicals, and heterocyclic radicals substituted with non-interfering substituents;

$R^{4'}$ is selected from groups (a) and (b) where;
  (a) is —$(C_5-C_{20})$alkyl, —$(C_5-C_{20})$alkenyl, —$(C_5-C_{20})$alkynyl, carbocyclic radicals, or heterocyclic radicals, or
  (b) is a member of (a) substituted with one or more independently selected non-interfering substituents;

or a pharmaceutically acceptable racemate, solvate, optical isomer, prodrug derivative or salt thereof.

19. A method of treating a condition selected from the group consisting of sepsis, septic shock, adult respiratory distress syndrome, pancreatitis, trauma-induced shock, asthma, rheumatoid arthritis, osteoarthritis, acute bronchitis, chronic bronchitis, Inflammatory Bowel Disease, apoptosis, stroke, cystic fibrosis, allergic rhinitis, acute bronchiolitis, chronic bronchiolitis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and join), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a subject in need of such treatment, a therapeutically effective amount of a compound of formula II

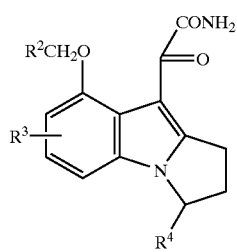

(II)

wherein;
$R^2$ is —$CO_2H$, —$CO_2(C_1-C_4$ alkyl);

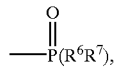

tetrazolyl —$CONR^9R^{10}$; —$SO_2R^{15}$, —$CONHSO_2R^{15}$, or phenyl substituted with —$CO_2H$ or —$CO_2(C_1-C_4)$ alkyl, where $R^6$ and $R^7$ are each independently —OH or —$O(C_1-C_4)$alkyl, $R^9$ and $R^{10}$ are each independently hydrogen, —$CF_3$, —$(C_1-C_4)$alkyl, phenyl or —$(C_1-C_4)$alkylphenyl and $R^{15}$ is hydrogen, aryl, —$(C_1-C_6)$alkyl or —$CF_3$;

$R^3$ is hydrogen, —$O(C_1-C_4)$alkyl, halo, —$(C_1-C_6)$alkyl, phenyl, —$(C_1-C_4)$alkylphenyl; phenyl substituted with —$(C_1-C_6)$alkyl, halo, or —$CF_3$; —$CH_2OSi(C_1-C6)_3$alkyl, furyl, thiophenyl, —$(C_1-C_6)$hydroxyalkyl, —$(C_1-C_6)$alkoxy$(C_1-C6)$alkyl, —$(C_1-C_6)$alkoxy$(C_1-C_6)$alkenyl, —$(C_1-C_6)$alkoxy$(C_1-C_6)$alkyl, —$(C_1-C_6)$alkoxy, —$(C_1-C_6)$alkenyl, or —$(CH_2)_nR^8$, where $R^8$ is hydrogen, —$CONH_2$, —$NR^9R^{10}$, —CN or phenyl, where $R^9$ and $R^{10}$ are independently hydrogen, —$CF_3$, phenyl, —$(C_1-C_4)$alkyl or —$(C_1-C_4)$alkylphenyl and n is 1 to 8; and $R^4$ is —$(C_5-C_{14})$alkyl, —$(C_3-C_{14})$cycloalkyl, pyridyl, phenyl or phenyl substituted with —$(C_1-C_6)$alkyl, halo, —$CF_3$, —$OCF_3$, —$(C_1-C_4)$alkoxy, —CN, —$(C_1-C_4)$alkylthio, phenyl $(C_1-C_4)$alkyl, —$(C_1-C_4)$alkylphenyl, phenyl, phenoxy or naphthyl;

or a pharmaceutically acceptable racemate, solvate, optical isomer, prodrug derivative or salt, thereof.

20. A method of claim 13 wherein the condition is sepsis, septic shock, adult respiratory distress syndrome, pancreatitis, trauma-induced shock, asthma, rheumatoid arthritis, osteoarthritis, acute bronchitis, chronic bronchitis or Inflammatory Bowel Disease.

21. A method of claim 14 wherein the condition is sepsis, septic shock, adult respiratory distress syndrome, pancreatitis, trauma-induced shock, asthma, rheumatoid arthritis, osteoarthritis, acute bronchitis, chronic bronchitis or Inflammatory Bowel Disease.

* * * * *